(12) United States Patent
Iijima et al.

(10) Patent No.: US 6,429,308 B1
(45) Date of Patent: Aug. 6, 2002

(54) HIV INFECTION INHIBITORS

(75) Inventors: Osamu Iijima; Takeshi Goto, both of Tsukuba; Takashi Shimada, Tokyo, all of (JP)

(73) Assignee: Hisamitsu Pharmaceutical Co., Inc., Saga (JP)

( * ) Notice: Subject to any disclaimer, the term of this patent is extended or adjusted under 35 U.S.C. 154(b) by 0 days.

(21) Appl. No.: 09/582,224

(22) PCT Filed: Nov. 24, 1999

(86) PCT No.: PCT/JP99/06534

§ 371 (c)(1),
(2), (4) Date: Jul. 21, 2000

(87) PCT Pub. No.: WO00/31271

PCT Pub. Date: Jun. 2, 2000

(30) Foreign Application Priority Data

Nov. 24, 1998 (JP) .......................................... 10/332760

(51) Int. Cl.⁷ ........................ C07H 21/04; C07H 21/02; C12Q 1/68; C12P 19/34; C12N 15/63

(52) U.S. Cl. ........................ 536/24.5; 435/6; 435/91.1; 435/455; 435/458; 536/23.1

(58) Field of Search ........................... 435/6, 91.1, 91.5, 435/375, 455, 366; 514/44; 536/23.1, 24.5

(56) References Cited

PUBLICATIONS

W. James, Towards gene–inhibition therapy: a review of progress and prospects in the field of antiviral antisense nucleic acids and ribozymes, Antiviral Chemistry & Chemotherapy (1991) 2(4) pp. 191–214.*
Karen Pihl–Carey, Isis To Restructure As Crohn's Disease Drug Falls In Phase III, BioWorld Today, Dec. 15, 1999 vol. 10, No. 239 pp. 1–2.*
Andrea D. Branch, A good antisense molecule is hard to f ind, TIBS Feb. 23, 1998, pp. 45–50.*
Natalie Milner et al., Selecting effective antisense reagents on combinatorial oligonucleotide arrays, Nature Biotechnology vol. 15 Jun. 1997 pp. 537–541.*
Giorgio Palu' et al., In pursuit of new developments for gene therapy of human diseases, Journal of Biotechnology 68 (1999) pp. 1–13.*
Stanley T. Crooke, Antisense Research and Application, pp. 1–50.*

* cited by examiner

Primary Examiner—Andrew Wang
Assistant Examiner—Jane Zara
(74) Attorney, Agent, or Firm—Townsend and Banta

(57) ABSTRACT

An antisense oligonucleotide characterized in that it hybridizes specifically with chromosomal DNA and/or RNA encoding CXCR4 protein to thereby inhibit the expression of the CXCR4 protein, and a HIV infection inhibitor comprising the antisense oligonucleotide, are disclosed.

2 Claims, 1 Drawing Sheet

SEQUENCE LISTING

<160> NUMBER OF SEQ ID NOS: 5

<210> SEQ ID NO 1
<211> LENGTH: 24

-continued

```
<212> TYPE: DNA
<213> ORGANISM: Artificial Sequence
<220> FEATURE:
<223> OTHER INFORMATION: corresponding to from +67 to +90 of SEQ LIST
      NO:5

<400> SEQUENCE: 1
ctgatcccct ccatggtaac cgct                                              24

<210> SEQ ID NO 2
<211> LENGTH: 24
<212> TYPE: DNA
<213> ORGANISM: Artificial Sequence
<220> FEATURE:
<223> OTHER INFORMATION: corresponding to from +73 to +96 of SEQ LIST
      NO:5

<400> SEQUENCE: 2
tatatactga tcccctccat ggta                                              24

<210> SEQ ID NO 3
<211> LENGTH: 23
<212> TYPE: DNA
<213> ORGANISM: Artificial Sequence
<220> FEATURE:
<223> OTHER INFORMATION: corresponding to from +61 to +83 of SEQ LIST
      NO:5

<400> SEQUENCE: 3
cctccatggt aaccgctggt tct                                               23

<210> SEQ ID NO 4
<211> LENGTH: 24
<212> TYPE: DNA
<213> ORGANISM: Artificial Sequence
<220> FEATURE:
<223> OTHER INFORMATION: synthesized DNA in which the sequence according
      to SEQ LIST NO:1 was shuffled

<400> SEQUENCE: 4
aactcccttg gtgctcctac acgc                                              24

<210> SEQ ID NO 5
<211> LENGTH: 1664
<212> TYPE: DNA
<213> ORGANISM: Artificial Sequence
<220> FEATURE:
<223> OTHER INFORMATION: cDNA of CXCR4

<400> SEQUENCE: 5
cggcagcagg tagcaaagtg acgccgaggg cctgagtgct ccagtagcca ccgcatctgg        60
agaaccagcg gttaccatgg agggatcag tatatacact tcagataact acaccgagga       120
aatgggctca gggactatg actccatgaa ggaaccctgt ttccgtgaag aaaatgctaa       180
tttcaataaa atcttcctgc ccaccatcta ctccatcatc ttcttaactg gcattgtggg       240
caatggattg gtcatcctgg tcatgggtta ccagaagaaa ctgagaagca tgacggacaa       300
gtacaggctg cacctgtcag tggccgacct cctctttgtc atcacgcttc ccttctgggc       360
agttgatgcc gtggcaaact ggtactttgg gaacttccta tgcaaggcag tccatgtcat       420
ctacacagtc aacctctaca gcagtgtcct catcctggcc ttcatcagtc tggaccgcta       480
cctggccatc gtccacgcca ccaacagtca gaggccaagg aagctgttgg ctgaaaaggt       540
ggtctatgtt ggcgtctgga tccctgccct cctgctgact attcccgact tcatctttgc       600
```

```
                                                    -continued caacgtcagt gaggcagatg acagatatat ctgtgaccgc ttctacccca atgacttgtg    660
ggtggttgtg ttccagtttc agcacatcat ggttggcctt atcctgcctg gtattgtcat    720
cctgtcctgc tattgcatta tcatctccaa gctgtcacac tccaagggcc accagaagcg    780
caaggccctc aagaccacag tcatcctcat cctggctttc ttcgcctgtt ggctgcctta    840
ctacattggg atcagcatcg actccttcat cctcctggaa atcatcaagc aagggtgtga    900
gtttgagaac actgtgcaca agtggatttc catcaccgag gccctagctt tcttccactg    960
ttgtctgaac cccatcctct atgctttcct tggagccaaa tttaaaacct ctgcccagca   1020
cgcactcacc tctgtgagca gagggtccag cctcaagatc ctctccaaag gaaagcgagg   1080
tggacattca tctgtttcca ctgagtctga gtcttcaagt tttcactcca gctaacacag   1140
atgtaaaaga cttttttta tacgataaat aactttttt taagttacac attttcaga     1200 tataaaagac tgaccaatat tgtacagttt ttattgcttg ttggatttt gtcttgtgtt   1260 tctttagttt ttgtgaagtt taattgactt atttatataa attttttttg tttcatattg  1320
atgtgtgtct aggcaggacc tgtggccaag ttcttagttg ctgtatgtct cgtggtagga   1380
ctgtagaaaa gggaactgaa cattccagag cgtgtagtta atcacgtaaa gctagaaatg   1440
atccccagct gtttatgcat agataatctc tccattcccg tggaacgttt ttcctgttct   1550
taagacgtga ttttgctgta gaagatggca cttataacca aagcccaaag tggtatagaa   1560
atgctggttt ttcagttttc aggagtgggt tgatttcagc acctacagtg tacagtcttg   1620
tattaagttg ttaataaaag tacatgttaa acttaaaaaa aaaa                   1664
```

HIV INFECTION INHIBITORS

The present application hereby claims priority under 35 U.S.C. 119 of the Japanese application No. 10/332760, filed Nov. 24, 1998.

TECHNICAL FIELD

The present invention relates to an antisense oligonucleotide against chromosomal DNA and/or RNA encoding CXCR4 protein and an HIV infection inhibitor containing the antisense oligonucleotide. More specifically, the present invention relates to an antisense oligonucleotide which can inhibit the HIV infection, by hybridizing specifically with the chromosomal DNA and/or RNA of the CXCR4 protein, being a receptor of the cell side concerning AIDS infection, to thereby inhibit the expression thereof, and an HIV infection inhibitor containing the antisense oligonucleotide.

BACKGROUND ART

The AIDS is a disease which is induced by human immunodeficiency virus (HIV) infection, injures cellular immunity greatly to thereby cause many kinds of opportunistic infections, lymphoma, neuropathy, or the like, and finally death certainly.

As the present remedy, a reverse transcriptase inhibitor such as azidothymidine (AZT), dideoxy inosine (ddI), dideoxy cytidine (ddC), or a protease inhibitor such as saquinavir, ritonavir, indinavir is used alone or in combination (Hammner, S. M. et al., New Engl. J. Med., 335, 1081–1090,1996). The nucleotide reverse transcriptase inhibitor inhibits the integration of virus into chromosome, by acting in the step when the reverse transcriptase of the virus itself transcripts the gene information of the virus from RNA into DNA after HIV enters cells. However, there is some case where resistant viruses are appeared by a long-term administration of these reverse transcriptase inhibitor and protease inhibitor, and thus the drugs become unavailable (Shirasaka, T. et al., Proc. Natl. Acad. Sci. USA, 92,2398–2402, 1995;Condra, J. H. et al., Nature, 374, 569–571, 1995). Further, since it causes disorders on DNA metabolism on the cell side, many side effects such as anemia, decrease of the number of leukocytes, nausea, head ache, malaise, stupor, myositis due to the long-term administration, have been reported. Thus developments of a new therapy have been desired strongly.

The main target cells of the HIV are CD4-positive T cell and macrophage. The HIV can be divided greatly into three kinds: a strain which infects CD4 positive T cell and does not infect macrophage (T cell tropic HIV), a strain which infects macrophage and does not infect CD4 positive T cell (macrophage tropic HIV), and a strain which can infect both cells (both tropic HIV) . From the past, as a receptor of the HIV on the cell side, CD4 has been known, but the second receptor concerning the T cell-tropic characteristics of the HIV was identified in 1996, and named CXCR4 (Feng, Y., et al., Science, 272, 872–877(1996)). In addition, at the same time, as a second receptor of the macrophage tropic HIV, CCR5 was identified (Alkhatib, G. et al., Science, 272, 1955–1958, 1996). These second receptors are indispensable factors on the cell side for HIV for infection as well as CD4, but these are primarily a receptor against chemokine secreted in living organisms. The fact that the ligand of the CXCR4 is SDF1, the ligand of CCR5 is MIP-1α, MIP-1β and RANTES, are shown.

As to the therapy for HIV infectious diseases, many reports have been made from the past. However, since the mutation of genomic gene of HIV occurred in a very high rate compared with genomic gene of cell derived from mammal animals, there is a disadvantage that, even if a drug effective on HIV specifically is invented, the drug becomes ineffective on a mutated HIV. To the course of the study on the factors on the HIV side, some experiments have been made to treat the HIV infectious diseases by controlling the factors on the cell side concerning the HIV infections. With the method, since mutation of the genomoc gene of cells rarely occurs, there is a few possibility that the drug becomes unavailable by appearing a resistant virus which is shown in reverse transcriptase inhibitor. In addition, the conventional anti-HIV drug acts on virus itself after infecting on cells, on the other hand, this method inhibits the infection step of HIV, so that the HIV does not enter cells themselves, and there is a few possibility of injuring the viability and functions of the cell.

In recent years, many basic studies on the therapy of the HIV infectious disease directed to these second receptors, have been reported. For examples, the fact that SDF1, MIP-1α, MIP-1β and RANTES inhibit the T cell tropic HIV and macrophage tropic HIV infections in a way of a competitive inhibition by competiting receptors (Bleul, C. C., et al., Nature, 829–833, 1996; Cocchi, F., et al., Science, 270,1811–1815, 1995), the fact that the antagonist inhibits the HIV infection, and a method of not expressing a receptor on the surface of a cell by expressing chemokine within a target cell excessively (Chen, J. D., et al., Nature Medicine, 3, 1110–1116, 1997), are considered. However, the large amount of chemokine administration stimulates the HIV infectious cells to thereby possibly release a large amount of HIV (Schmidtmayerova, H., et al., Nature, 382, 767, 1996). Thus when it is to be applied practically in therapy, there is a doubt in its effects.

The present invention was made in view of the above circumstances, and the object of the invention is to provide an antisense oligonucleotice which can inhibit the HIV infection to thereby prevent and treat the AIDS infection by inhibiting the CXCR4 protein expression of the target cell when infected with HIV, and an HIV infection inhibitor containing the antisense oligonucleotide.

DISCLOSURE OF THE INVENTION

The present inventors researched earnestly in order to dissolve the above problems, and as the results, succeeded in finding antisense gene sequences which inhibit specifically the CXCR4 protein expression to thereby inhibit the infection of HIV into cells, and completed the present invention.

Thus, the present inventors, as an antisense oligonucleotide inhibiting specifically the CXCR4 protein expression, considered the gene encoding the CXCR4 protein as a target gene, and examined repeatedly in view of the facts that the coding region, G cap region, initiation codon region or the like may possibly hybridize (Takeuchi, K., et al., Experimental Medicine, 573–583, 1996), and they selected the initiation codon region of the CXCR4 so as to complete the present invention.

Namely, the present invention comprises an antisense oligonucleotide characterized in that it hybridizes specifically with the chromosomal DNA and/or RNA encoding CXCR4 protein to thereby inhibit the CXCR4 protein expression, and it has one or more of the following sequences (A) to (C):
(A) the sequence described in the SEQ ID NO:1 in the SEQUENCE LISTING,
(B) the sequence described in the SEQ ID NO:2 in the SEQUENCE LISTING,
(C) the sequence described in the SEQ ID NO:3 in the SEQUENCE LISTING.

Further, the present invention comprises an HIV infection inhibitor containing the above antisense oligonucleotide.

BEST MODE FOR CARRYING OUT THE INVENTION

Figure 1:
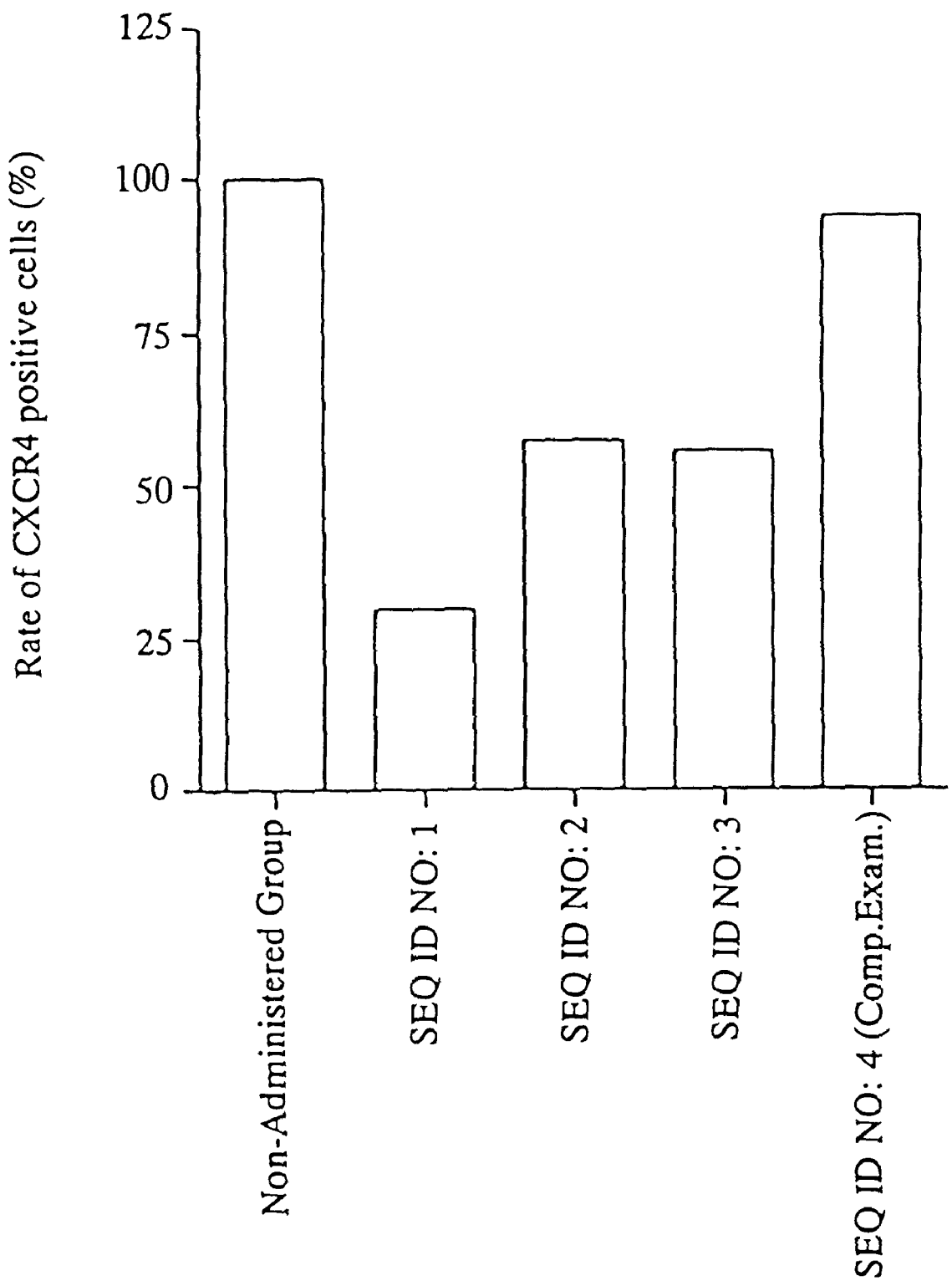
FIG. 1 is a graph showing the effects on inhibition of the CXCR4 protein expression of the antisense oligonucleotides of the present invention.

The present invention will be explained in detail, hereinafter.

The antisense oligonucleotide of the present invention is an antisense oligonucleotide which is complementary to some parts of base sequences of chromosomal DNA and/or RNA encoding CXCR4 protein. The antisense oligonucleotide of the present invention may be DNA or RNA.

The antisense oligonucleotide of the present invention is complimentary to the base sequence containing initiation codon region from +61 to +91 when the gene transcription initiation point of mRNA encoding CXCR4 protein is to be +1, and at the same time hybridizes stably with the said sequence specifically and blocks the translation into a protein so as to have a function to inhibit the biosynthesis of the CXCR4 protein.

The antisense oligonucleotide of the present invention contains any one or more of the sequences described in the SEQ LIST NOS:1 to 3 in the SEQUENCE LISTING, and more preferably contains the SEQ LIST NO:1. In addition, most preferably, the antisense oligonucleotide of the present invention contains the SEQ LIST NO: 1 and the initiation codon in the central of the sequence. The sequences described in the SEQ LIST NOS:1 to 3 show the antisense DNA strands of the CXCR4 protein gene. The SEQ LIST NO:1 corresponds to +67 to +90 of gene sequence of cDNA of the CXCR4 protein described in the SEQ LIST NO:5 (Nomura, H., et al., Int. Immunol., 5, 1239–1249, 1993), the SEQ LIST NO:2 similarly corresponds to +73 to +96 of the SEQ LIST NO:5, and the SEQU LIST NO:3 similarly corresponds to +61 to +83 of the SEQ LIST NO:No.5, respectively. Further, the SEQ LIST NO:1 contains an initiation codon of the CXCR4 protein gene in the central of the antisense DNA strand, the SEQ LIST NO:2 similarly contains an initiation codon of the CXCR4 protein gene in the 3' side of the antisense DNA strand, and the SEQ LIST NO:3 similarly contains an initiation codon of the CXCR4 protein gene in the 5' side of the antisense DNA strand, respectively.

The upper limit of the length of the antisense oligonucleotide of the present invention is preferably 100 bases or less, and more preferably 30 bases or less, from the reason that the gene synthesis efficiency using a DNA/RNA synthesizer decreases with the increase of base number and in view of cost for synthesis. The lower limit of the length of the gene is preferably 8 base or more, more preferably 12 base or more, and most preferably 15 base or more in order to keep the specific of the antisense oligonucleotide.

The method of synthesizing antisense olibonucleotide of the present invention is not particularly limited, for example, the oligonucleotide of phosphorothioate type or phosphotriester type can be obtained with a phosphoramidite method using a conventional origonucleotide synthesizer. As examples of the antisense oligonucleotide obtained by these synthesizing method, origonucleotide of phosphodiester type, oligonucleotide of phosphorothioate type in which phosphate group is modified by a covalent bond with a sulfur atom in order to avoid the degradation by nuclease when administered in a living organism, methylphosphonate type oligonucleotide in which phosphate backbone is methylated, morpholine backbone oligonucleotide in which morpholine is transferred in place of the phosphate backbone, oligonucleotide which is modified with fat-soluble geraniol in order to increase membrane permeable or the like, are exemplified.

The antisense oligonucleotide of the present invention can be used as an HIV infection inhibitor. In this case, the antisense oligonucleotide of the present invention can be used alone, but can be transferred into a target cell securely to be used as a composition in which it is combined with a pharmaceutically acceptable carrier in order to avoid degradation in an living organism. The carrier is not particularly limited so long as being a pharmaceutical acceptable material, but a high molecular material having a positive electric charge, liposome, microsphere or the like may be used preferably.

As the high molecular materials having a positive electric charge, TfX-50 (-10, -20) (manufactured by Promega), Transfectam (manufactured by Wako Junyaku Kogyo Co., Ltd.), ExGen 500 (manufactured by Wako Junyaku Kogyo co., Ltd.), synthesized polyamino acid or an derivative thereof, e.g., Poly-lysine:serine (PLS) disclosed in WO95/09009 publication, PEG block modified PLS disclosed in Japanese Un-examined patent publication No. 9-176038, etc., may be exemplified.

As the liposome, LIPOFECTIN (manufactured by GIBCO), Lipofect AMINE (manufactured by GIBCO), CellFECTIN (manufactured by GIBCO), DMRIE-C (manufactured by GIBCO) or the like, may be exemplified. As the microsphere, SuperFect (manufactured by QIAGEN) or the like may be exemplified. These pharmaceutically acceptable carrier and the antisense oligonucleotide of the present invention can be formed into a complex by means of a known method.

The methods of using the antisense oligonucleotide and the HIV infection inhibitor of the present invention are not particularly limited, and may be used in vivo, in vitro, ex vivo or the like. The antisense oligonucleotide of the invention may be used as an antisense RNA expression construct for gene therapy, by inserting it into a gene expression vector containing a gene sequence promoting gene expression. As the gene expression vector, a plasmid, a recombinant virus or the like may be used.

If a plasmid is selected as a gene expression vector, it can be used alone, but preferably used in a composition in which a complex is formed with a pharmaceutically acceptable carrier in order to avoid the degradation by nuclease and to improve the gene expression efficiency. In addition, the recombinant virus can be used without particular limitation, so long as being infectious for a cell derived from mammal animals, preferably from human. The recombinant virus maybe selected from murine leukemia virus, adenovirus, adeno-associated virus, human immunodeficiency virus, Sindbis virus, herpes virus, Sendai virus and Epstein-Barr virus. Among them, murine leukemia virus, adenovirus, adeno-associated virus and human immunodeficiency virus are preferable, and human immunodeficiency virus is most preferable. The method of using the antisense RNA expression construct is not particularly limited, and may be used in vivo, in vitro, ex vivo or the like.

EXAMPLES

The present invention will be described in more detail by way of Examples. However, these Examples are shown only to assist the understanding of the present invention, and not to limit the scope of the invention.

Example 1

Synthesis and Purification of Antisense Oligonucleotide

As to the antisense oligonucleotides according to the SEQ ID NOS:1 to 3 of the SEQUENCE LISTING and the DNA strand of SEQ ID NO:4, phosphorothioate types were synthesized by a phosphoamidide method using a DNA synthesizer, and these were further purified under a known condition using an ion-exchange FPLC (committed Amersham Pharmacia Biotech).

The sequences according to the SEQ ID NOS:1 to 3 are antisense DNA strands of the CXCR4 protein genes. The SEQ ID NO:1 corresponds to from +67 to +90 of the SEQ ID NO:5, the SEQ ID NO:2 corresponds to from +73 to +96 of the SEQ ID NO:5, and the SEQ ID NO:3 corresponds to from +61 to +83 to SEQ ID NO:5, respectively.

The SEQ ID NO:5 shows the base sequence of cDNA of CXCR4 protein (Nomura, H., et al., Int. Immunol., 5,1239–1249, 1993).

In addition, the SEQ ID NO:4 comprises 24 bases whose length is essentially identical to those of the SEQ ID NOS:1 to 3, and is a synthesized DNA strand of a negative control group in which the sequence of the SEQ ID NO:1 was shuffled so as to have the same content of A, C, G and T as that of the SEQ ID NO:1. (Comparative Example)

Example 2

Preparation of a Complex of Antisense Oligonucleotide and Transfection Reagent (HIV Infection Inhibitor)

The DMRIE-C reagent manufactured by GIBCO was used as a transfection agent (pharmaceutical acceptable carrier). The antisense oligonucleotides according to the SEQ ID NOS: 1 to 3 were prepared in a concentration of 2 $\mu$M in 500 $\mu$l Opti-MEM medium (manufactured by GIBCO), respectively to obtain A liquid. Further, the DMRIE-C reagent was prepared in a concentration of 20 $\mu$g/ml in 500 $\mu$l of Opti-MEM medium to obtain B liquid. By leaving to stand for 30 minutes after adding B liquid to A liquid and stirring gently, an antisense oligonucleotide/DMRIE-C complex was obtained. In addition, as a comparative Example, a similar complex was obtained using the DNA strand of the SEQ ID NO:4.

Test Example 1

Test of Effects on Inhibition of CXCR4 Protein Expression (A) Transfer of the Antisense Oligonucleotide Into Culture Cells The inhibition effects on the CXCR4 proteins expression of the antisense oligonucleotides of the SEQ ID NOS:1 to 3 and the DNA strand of the SEQ ID NO:4, were examined in culture cell lines.

As the cells, the HeLa cells in which a gene encoding the CD4 protein is integrated so as to express endogenous CXCR4 proteins constantly and to express the CD4 protein constantly, were used (these were referred as "CD4 HeLa cells", hereinafter) . The CD4 HeLa cells were kept under the conditions of 37° C., 5%$CO_2$, in a Dulbecco's Modified Eagle's medium (DMEM: manufactured by GIBCO) added by 10% fetal bovine serum (FCS: manufactured by GIBCO) and an antibiotics.

After seeding the CD4 HeLa cells to have a concentration of 5×10$^5$/well in a 6 well plate and culturing for one night, the cells were washed with the Opti-MEM twice, and 1 ml of the antisense oligonucleotide/DMRIE-C complex prepared in Example 2 was added. After culturing under the conditions of 37° C., 5%$CO_2$ for four hours, 5 ml of DMEM containing 10% FCS was added, and further cultured under the conditions of 37° C., 5%$CO_2$.

(B) Detection of CXCR4 Protein by Florescent Antibody Technique

The cells in which antisense oligonucleotide was transferred in the above (A), was collected after 24 hours and treated with a monoclonal antibody against CXCR4 (manufactured by PHARMINGEN), and then stained with a FITC-labeled secondary antibody (manufactured by Jackson ImmunoResearch). The rate of the CXCR4 positive cells in the stained cells was analyzed using FACS Calibur flow site meter (manufactured by Becton Dickinson). The results were shown in FIG. 1.

With the antisense oligonucleotide non-administered group and the SEQ ID NO:4 (Comparative Example), the rates of the CXCR4-positive cells were not changed for 24 hours culture period. On the other hand, with the antisense oligonucleotides of SEQ ID NOS:1 to 3 administered group, the rates of the CXCR4-positive cells were greatly decreased for 24 hours culture period. In particular, the antisense oligonucleotide of the SEQ ID NO:1 containing translation initiation codon in the central of antisense DNA strand, most decreases the rate of CXCR4-positive cells. From the results, it was proven that the antisense oligonucleotide of the present invention is very excellent in the effects on inhibition of the CXCR4 protein expression.

INDUSTRIAL APPLICABILITY

As described above, the antisense oligonucleotide of the present invention can inhibit the expression of the CXCR4 protein to thereby inhibit HIV infection. Therefore, The antisense oligonucleotide and the HIV infection inhibitor of the present invention are very effective as prophylactic and therapeutic drugs.

What is claimed is:

1. An in vitro HIV infection inhibiting composition comprising:
   an HIV infection inhibitor containing an antisense oligonucleotide defined by SEQ ID NO: 1, SEQ ID NO: 2 or SEQ ID NO: 3;
   wherein said antisense oligonucleotide hybridizes specifically with a nucleic acid encoding CXCR4 protein to thereby inhibit the expression of CXCR4 protein.

2. The composition of claim 1, further comprising a pharmaceutically acceptable carrier, said pharmaceutically acceptable carrier selected from the group consisting of TFX-50, TRANSFECTAM, EXGEN 500, synthesized polyamino acid or a derivative thereof, serine, PEG block modified PLS, a liposome and a microsphere.

* * * * *